United States Patent [19]

Hoke

[11] 3,979,441

[45] Sept. 7, 1976

[54] OIL-SOLUBLE POLYMERS OF N-3-AMINOALKYL ACRYLAMIDES, AND LUBRICANTS CONTAINING THEM

[75] Inventor: Donald Irvin Hoke, Chagrin Falls, Ohio

[73] Assignee: The Lubrizol Corporation, Cleveland, Ohio

[22] Filed: Mar. 27, 1974

[21] Appl. No.: 455,162

Related U.S. Application Data

[60] Continuation-in-part of Ser. Nos. 237,871, March 24, 1972, Pat. No. 3,856,689, and Ser. No. 203,853, Dec. 1, 1971, Pat. No. 3,883,491, said Ser. No. 237,871, is a continuation-in-part of Ser. No. 832,412, June 11, 1969, Pat. No. 3,666,810, said Ser. No. 203,853, is a division of Ser. No. 832,412.

[52] U.S. Cl. ............................. 260/482 R; 252/51; 260/247.2 B; 260/295 AM; 260/309; 260/310 R; 260/326.14 R; 260/326.2; 260/326.85; 260/468 J; 260/470; 260/471 A; 260/558 P; 260/561 N; 260/583 H

[51] Int. Cl.$^2$ ........................................ C07C 101/24
[58] Field of Search .................... 260/486 R, 482 R

[56] References Cited

UNITED STATES PATENTS

| | | | |
|---|---|---|---|
| 3,445,441 | 5/1969 | Rushton | 260/486 R |
| 3,514,250 | 5/1970 | Rushton | 260/486 R |

*Primary Examiner*—Paul J. Killos
*Attorney, Agent, or Firm*—James W. Adams, Jr.; William H. Pittman

[57] ABSTRACT

Oil-soluble polymers of N-3-aminoalkyl acrylamides, especially N-(1,1-dimethyl-3-dimethylaminopropyl)acrylamide, are obtained by copolymerization with a monomer (especially an alkyl acrylate or methacrylate) containing an alkyl group with at least about 8 carbon atoms. These polymers are useful as dispersants and viscosity modifiers for lubricants.

7 Claims, No Drawings

OIL-SOLUBLE POLYMERS OF N-3-AMINOALKYL ACRYLAMIDES, AND LUBRICANTS CONTAINING THEM

This application is a continuation-in-part of copending applications Ser. No. 237,871, filed Mar. 24, 1972, now U.S. Pat. No. 3,856,689, and Ser. No. 203,853, filed Dec. 1, 1971, now U.S. Pat. No. 3,883,491. Ser. No. 237,871 is a continuation-in-part and Ser. No. 203,853 a division of application Ser. No. 832,412, filed June 11, 1969, now U.S. Pat. No. 3,666,810.

This invention relates to new polymeric compositions of matter and lubricants containing them. More specifically, it relates to oil-soluble interpolymers comprising (A) at least about 50% by weight of units derived from a polymerizable unsaturated monomer containing an alkyl group with at least about 8 carbon atoms, said interpolymer also containing (B) units derived from a monomer of the formula

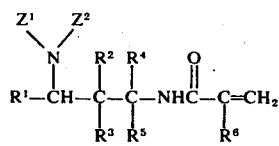

wherein each of $R^1$, $R^2$ and $R^3$ is hydrogen or a hydrocarbon or substituted hydrocarbon radical; each of $R^4$ and $R^5$ is a hydrocarbon or substituted hydrocarbon radical; $R^6$ is hydrogen or a lower alkyl or substituted lower alkyl radical; $Z^1$ is a hydrogen or a hydrocarbon or substituted hydrocarbon radical and $Z^2$ is hydrogen or an alkyl, cycloalkyl or substituted alkyl or cycloalkyl radical, or

is a heterocyclic radical.

The demands made on lubricants for internal combustion engines and the like are constantly becoming greater and it is of continuing interest to develop new additive compositions for said lubricants which combine a variety of beneficial properties and perform them more efficiently than known additives. In particular, increasing interest has developed in recent years in the production of lubricant additives which combine viscosity modifying properties with dispersant properties. Many of these additives are polymeric in nature.

A principal object of the present invention, therefore, is to provide new polymeric compositions of matter suitable for use as lubricant additives.

A further object is to provide compositions of matter which impart viscosity improving and dispersant properties to lubricants.

Still another object is to provide new lubricants which have improved viscosity and dispersant properties as compared with known lubricants.

Other objects will in part be obvious and will in part appear hereinafter.

As previously described, the oil-soluble interpolymers of this invention comprise units of two different types, designated as A and B. The A units, which comprise at least about 50% and preferably at least about 75% of the polymer (by weight), are derived from a polymerizable unsaturated monomer containing an alkyl group with at least about 8 carbon atoms; especially suitable are alkyl esters of unsaturated acids, the alkyl group in said ester containing at least about 8 carbon atoms, such as $C_{12-14}$ dialkyl fumarate, $C_{12-14}$ dialkyl maleate, 2-ethylhexyl acrylate, isodecyl acrylate and dodecyl methacrylate. The alkyl acrylates and methacrylates of this description are especially preferred.

The B units in the oil-soluble interpolymers of this invention are derived from an aminoalkyl acrylamide having the above formula. The term "hydrocarbon radical", as used in the definition of these compounds, includes aliphatic, cycloaliphatic and aromatic (including aliphatic- and cycloaliphatic-substituted aromatic and aromatic-substituted aliphatic and cycloaliphatic) radicals. It also includes cyclic radicals wherein the ring is completed through another portion of the molecule; that is, any two indicated substituents may together form a cycloalkyl radical.

The following are illustrative of hydrocarbon radicals within the scope of this invention. Where a named radical has several isomeric forms (e.g., butyl), all such forms are included.

| | |
|---|---|
| Methyl | Tolyl |
| Ethyl | Xylyl |
| Propyl | Benzyl |
| Butyl | Cyclohexyl |
| Hexyl | Cyclopentyl |
| Octyl | Methylcyclopentyl |
| Decyl | Cyclopentadienyl |
| Vinyl | Vinylphenyl |
| Allyl | Isopropenylphenyl |
| Ethynyl | Cinnamyl |
| Propargyl | Naphthyl |
| Phenyl | |
| —$C_6H_3(C_2H_5)_2$ | |
| —$C_6H_4(CH_2)_{11}CH_3$ | |

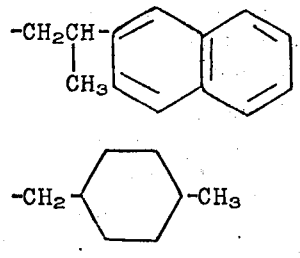

Many obvious variations of these radicals will be apparent to those skilled in the art and are included within the scope of the invention.

Substituted hydrocarbon, alkyl, aryl, etc., radicals are considered fully equivalent to the hydrocarbon, alkyl, aryl etc., radicals and to be part of this invention. By "substituted" is meant radicals containing substituents which do not alter significantly the character or reactivity of the radical. Examples are:
Halide (fluoride, chloride, bromide, iodide)
Hydroxy
Ether (especially lower alkoxy)
Keto
Ester (especially lower carbalkoxy)
Aminoacyl (amide)
Amino
Nitro
Cyano Mercapto
Thioether
Sulfoxy
Sulfone
Sulfonic acid esters and amides In general, no more than about three such substituent groups will be present for each 10 carbon atoms in the radical.

Preferably, the hydrocarbon or substituted hydrocarbon radicals in the compounds from which the B units are derived are free from ethylenic and acetylenic unsaturation and have no more than about 30 carbon atoms, desirably no more than about 12 carbon atoms. A particular preference is expressed for lower hydrocarbon radicals, the word "lower" denoting radicals containing up to seven carbon atoms. Still more preferably, they are lower alkyl or aryl radicals, most often alkyl.

In the especially preferred interpolymers, each of $R^{1-3}$ is a hydrogen or lower alkyl radical; each of $R^4$ and $R^5$ is a lower alkyl radical; $R^6$ is hydrogen or methyl; and $Z^1$ and $Z^2$ are lower alkyl radicals. Also within the scope of the invention, as previously noted, are polymers derived from compounds in which

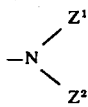

is a heterocyclic radical, typically one which is monocyclic or bicyclic and in which the only hetero-atoms are nitrogen (e.g., pyrrole, pyrrolidine, piperidine, indole, imidazole, pyrazole) or nitrogen and oxygen (e.g., morpholine). The heterocyclic radical may contain hydrocarbon (especially lower alkyl) or other substituents of the type described hereinabove.

The following are illustrative of compounds from which the B units may be derived.

N-(1,1-dimethyl-3-dimethylaminopropyl)acrylamide

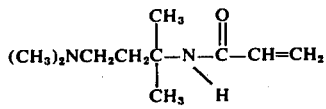

N-(1,1-dimethyl-3-dimethylaminobutyl)acrylamide

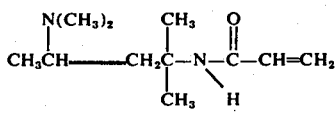

N-(1-methyl-1,3-diphenyl-3-diethylaminopropyl)methacrylamide

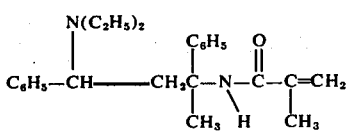

N-[1-methyl-1,3-(p-chlorophenyl)-3-pyrrolidinopropyl]acrylamide

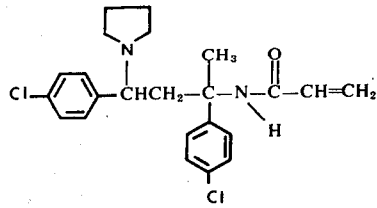

The compounds from which the B units are derived may be prepared by reacting an oxypropionamide of the formula

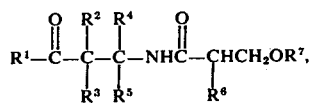

wherein $R^7$ is a hydrocarbon or substituted hydrocarbon radical and usually a lower alkyl (e.g., methyl) radical, with an amine of the formula

in the presence of a reducing agent, and subsequently eliminating $R^7OH$ from the intermediate thus obtained. Oxypropionamides of the above formula may be obtained by the reaction of a hydroxy compound (alcohol or phenol, preferably an alcohol) with an N-3-oxohydrocarbon-substituted acrylamide of the type disclosed in U.S. Pat. Nos. 3,277,056 and 3,425,942. The reaction leading to the oxypropionamide is disclosed in U.S. Pat. No. 3,647,875. The disclosures of these patents are incorporated by reference in the present specification.

The reaction of the oxypropionamide with the amine is of the type generally identified as "reductive amination". A typical example of such a reaction is the Leuckart reaction, in which an oxo compound is reacted with an amine in the presence of formic acid, or with an amine formate, with the result that the carbon atom formerly part of the oxo group is aminated and carbon dioxide and water are evolved as by-products.

A preferred method for reductive amination of the oxypropionamide involves its reaction with the amine in the presence of hydrogen and a hydrogenation catalyst such as platinum/platinum oxide, palladium, copper chromite or Raney nickel. Of these catalysts, platinum/platinum oxide (Adams' catalyst) is preferred. (It is referred to as "platinum/ platinum oxide" because it is usually introduced as the oxide, but is immediately reduced to elemental platinum upon contact with hydrogen.) Typically, the oxypropionamide and the amine are mixed and a small amount of the hydrogenation catalyst is added; the mixture is then pressurized with hydrogen to at least about 50 psi. and agitated, typically at a temperature of about 25°–100°C. and usually with periodic replenishment of the hydrogen pressure, until hydrogen uptake has ceased. The reductive amination may be effected in the presence of a suitable solvent such as an alcohol, ether or the like, but such solvent is frequently unnecessary. It has also been found that the presence of a small amount (usually about 0.1–5.0% by weight of the reaction mixture) of an acid increases the reaction rate. Typical acids which may be used are aromatic sulfonic acids, mineral acids, perchloric acid and amine salts thereof, and the like.

The molar ratio of amine to oxypropionamide in the reaction mixture should be at least 1:1, and is generally greater (up to about 5:1). Ratios between about 1.25:1 and 3:1 are preferred.

The intermediate produced as described above has the formula

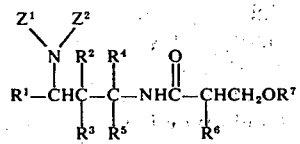

In the second step of the reaction sequence, $R^7OH$ is eliminated from this intermediate by any of several methods which are known per se. Typical methods are described briefly in a review: P. F. Butskus et al., *Russian Chemical Reviews*, 35, 39 (1966). The preferred method is pyrolysis in the presence of a basic reagent, ordinarily a strong base such as solid sodium hydroxide, at about 70°–150°C. This reaction is conveniently carried out at reduced pressure.

Another method for preparation of the compounds from which the B units are derived is by the reaction of a nitrile of the formula

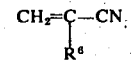

with an α,β-unsaturated amine of the formula

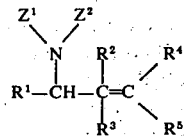

in the presence of sulfuric acid. Unsaturated amines of this type may be prepared by the reaction of a compound of the formula

with a 1,3-diene, usually in the presence of a strongly alkaline catalyst such as metallic sodium. This is a typical 1,4-addition reaction, known in the art.

For the reaction of the unsaturated amine with the nitrile, it is usually referred to use at least about 1.5 moles, typically about 1.9–3.0 moles, of the nitrile per mole of unsaturated amine. The sulfuric acid should be at least about 90%, and preferably 96–98%, in strength and the molar ratio of sulfuric acid to amine should be at least about 1:1, and preferably between about 1.1:1 and 2:1. Solvents are usually unnecessary, but it may be advantageous to add a small amount of a polymerization inhibitor such as hydroquinone, a hindered phenol or the like. When the reaction is complete, the product may be isolated by diluting and neutralizing the mixture and separating the unsaturated amide by traditional techniques.

The following examples illustrate the preparation of the compounds from which the B units are derived. All parts, percentages and proportions are by weight unless otherwise stated.

EXAMPLE 1

A one-gallon autoclave, fitted with a stirrer, is charged with 1684 parts (8.38 moles) of N-(1,1-dimethyl-3-oxobutyl)-3-methoxypropionamide, 762 parts (16.9 moles) of dimethylamine, 1.5 parts of platinum oxide and 15 parts of dimethylammonium perchlorate. The autoclave is pressurized with hydrogen to 750 psi., and stirring is begun. Hydrogen pressure is periodically restored to 850–900 psi. and stirring is continued until hydrogen uptake has ceased. Sodium bicarbonate, 10 parts, is added to the mixture which is then stripped, acidified, extracted with chloroform, made alkaline and again extracted with chloroform. The chloroform extract from the alkaline solution is stripped and distilled, and the product, N-(1,1-dimethyl-3-dimethylaminobutyl)-3-methoxypropionamide, is obtained boiling at 108°C./0.9 mm.

A mixture of 144.7 parts (0.63 mole) of N-(1,1-dimethyl-3-dimethylaminobutyl)-3-methoxypropionamide, 1 part of solid sodium hydroxide and 1 part of hydroquinone is charged to a reaction flask fitted with a condenser with a Dry Ice-cooled receiver, a stirrer and temperature control means. The pressure in the flask is reduced to less than 5 mm. and the flask is heated to 80°C. Vigorous reaction begins and liquid condenses in the receiver. After about one-half hour, the temperature is increased to 90°C. and this temperature is maintained for 3 hours. The product is distilled and the desired N-(1,1-dimethyl-3-dimethylaminobutyl)acrylamide is obtained at 80°–91°C./0.3–0.4 mm. The yield is 109.1 parts, or 87.4% of the theoretical amount, and the nitrogen percentage is the calculated 14.1%.

EXAMPLE 2

The procedure of Example 1 is repeated, except that the methoxypropionamide used therein is replaced by 325 parts (1 mole) of N-(1,3-diphenyl-1-methyl-3-oxopropyl)-3-methoxypropionamide. The product is N-(1,3-diphenyl-1-methyl-3-dimethylaminobutyl)acrylamide.

EXAMPLE 3

Following the procedure of Example 1, a mixture of 201 parts (1 mole) of N-(1,1-dimethyl-3-oxobutyl)-3-methoxypropionamide, 170 parts (2 moles) of piperidine, 0.5 parts of platinum oxide and 1 part of dimethylammonium perchlorate is hydrogenated in the Parr apparatus, starting at a pressure of 70 psi. and recharging when the pressure has reached 39 psi. The product is pyrolyzed with sodium hydroxide to yield the desired N-(1,1-dimethyl-3-piperidinobutyl)acrylamide.

EXAMPLE 4

The procedure of Example 1 is repeated, except that the dimethylamine is replaced by 1810 parts (16.9 moles) of methylaniline. The product is N-(1,1-dimethyl-3-methylanilinobutyl)acrylamide.

EXAMPLE 5

To a mixture of 273 parts (4 moles) of isoprene and 2 parts (0.087 mole) of sodium metal, at 0°C., is added 180 parts (4 moles) of dimethylamine over 1 hour. The temperature is maintained below 12°C. by cooling with a Dry Ice-isopropanol-filled cooling coil. After the dimethylamine addition is complete, the mixture is stirred and cooled for an additional 3½ hours. Methanol, 6 parts, is then added to decompose the sodium and the mixture is distilled. The fraction boiling at 117.5°–119.5°C. is the desired 1-dimethylamino-3-methyl-2-butene.

A resin flask is cooled to 0°C. and 450 grams (8.5 moles) of acrylonitrile, 1020 grams (10 moles) of sulfuric acid and 37 grams of water are added. To this mixture are then added 475 grams (4.2 moles) of the 1-dimethylamino-3-methyl-2-butene prepared as described above, and 8.5 grams of 2,6-di-t-butyl-p-cresol. The mixture is stirred at 68°C. for about 1 hour and is then neutralized with about 30% sodium hydroxide. The organic layer is separated, diluted with 2050 ml. of methanol and neutralized with ammonia. An additional 1000 ml. of methanol is added and the solution is filtered. The methanol is stripped from the filtrate and the residue is distilled. There is obtained 400 grams (64.5% of the theoretical amount) of the desired N-(1,1-dimethyl-3-dimethylaminopropyl)acrylamide boiling at 75°–92°C./0.25–0.9 mm. The nitrogen analysis is 15.4%, as compared with theoretical value of 15.2%.

The oil-soluble interpolymers of this invention are generally prepared by free radical polymerization in a relatively non-polar solvent such as benzene, toluene, cyclohexane, n-hexane, naphtha, tetrahydrofuran, mineral oil or the like. Typically, the polymerization temperature is about 0°–200°C.

The preparation of the oil-soluble interpolymers of this invention is illustrated by the following example.

EXAMPLE 6

A mixture of 640.2 parts of isodecyl acrylate, 19.8 parts of N-(1,1-dimethyl-3-dimethylaminopropyl) acrylamide and 440 parts of heptane is heated to 60°C. under nitrogen, with stirring, and 1.32 parts of azobisisobutyronitrile is added. An exothermic reaction causes the temperature to rise to 73°C. Heating is stopped and the mixture is cooled as polymerization takes place. It is held at 60°C. until polymerization is complete, and then oil is added and the heptane is removed by vacuum stripping to yield a 35% solution of the desired copolymer in oil.

The oil-soluble interpolymers of this invention can be employed in a variety of lubricating compositions based on diverse oils of lubricating viscosity, including natural and synthetic lubricating oils and mixtures thereof. The lubricating compositions contemplated included principally crankcase lubricating oils for spark-ignited and compression-ignited internal combustion engines including automobile and truck engines, two-cycle engine lubricants, aviation piston engines, marine and railroad diesel engines, and the like. However, automatic transmission fluids, transaxle lubricants, gear lubricants, metal-working lubricants, hydraulic fluids, and other lubricating oil and grease compositions can benefit from the incorporation of the polymers of this invention.

Natural oils include animal oils and vegetable oils (e.g., castor oil, lard oil) as well as solvent-refined or acid-refined mineral lubricating oils of the paraffinic, naphthenic, or mixed paraffinic-naphthenic types. Oils of lubricating viscosity derived from coal or shale are also useful base oils. Synthetic lubricating oils include hydrocarbon oils and halo-substituted hydrocarbon oils such as polymerized and interpolymerized olefins (e.g., polybutylenes, polypropylenes, propylene-isobutylene copolymers, chlorinated polybutylenes, etc.); alkylbenzenes (e.g., dodecylbenzenes, tetradecylbenzenes, dinonylbenzenes, di-(2-ethylhexyl)benzenes, etc.); polyphenyls (e.g., biphenyls, terphenyls, etc.); and the like. Alkylene oxide polymers and interpolymers and derivatives thereof where the terminal hydroxyl groups have been modified by esterification, etherification, etc., constitute another class of known synthetic lubricating oils. These are exemplified by the oils prepared through polymerization of ethylene oxide or propylene oxide, the alkyl and aryl ethers of these polyoxyalkylene polymers (e.g., methylpolyisopropylene glycol ether having an average molecular weight of 1000, diphenyl ether of polyethylene glycol having a molecular weight of 500–1000, diethyl ether of polypropylene glycol having a molecular weight of 1000–1500, etc.) or mono- and polycarboxylic esters thereof, for example, the acetic acid esters, mixed $C_3$-$C_8$ fatty acid esters, or the $C_{13}$ Oxo acid diester of tetraethylene glycol. Another suitable class of synthetic lubricating oils comprises the esters of dicarboxylic acids (e.g., phthalic acid, succinic acid, maleic acid, azelaic acid, suberic acid, sebacic acid, fumaric acid, adipic acid, linoleic acid dimer, etc.) with a variety of alcohols (e.g., butyl alcohol, hexyl alcohol, dodecyl alcohol, 2-ethylhexyl alcohol, pentaerythritol, etc.). Specific examples of these esters include dibutyl adipate, di(2-ethylhexyl)sebacate, di-n-hexyl fumarate, dioctyl sebacate, diisooctyl axelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles ot tetraethylene glycol and two moles of 2-ethylhexanoic acid, and the like. Silicon-based oils such as the polyalkyl-, polyaryl-, polyalkoxy-, or polyaryloxy-siloxane oils and silicate oils comprise another useful class of synthetic lubricants (e.g., tetraethyl silicate, tetraisopropyl silicate, tetra-(2-ethylhexyl) silicate, tetra-(4-methyl-2-tetraethyl) silicate, tetra-(p-tert-butylphenyl) silicate, hexyl-(4-methyl-2-pentoxy)-disiloxane, poly(methyl)-siloxanes, poly(methylphenyl)-siloxanes, etc.). Other synthetic lubricating oils include liquid esters of phosphorus-containing acids (e.g., tricresyl phosphate, trioctyl phosphate, diethyl ester of decane phosphonic acid, etc.), polymeric tetrahydrofurans, and the like.

In general, about 0.05–20.0 parts (by weight) of the polymer of this invention (excluding diluent) is dissolved in 100 parts of oil to produce a satisfactory lubricant. The invention also contemplates the use of other additives in combination with the products of this invention. Such additives include, for example, auxiliary detergents and dispersants of the ash-containing or ashless type, oxidation inhibiting agents, pour point depressing agents, extreme pressure agents, color stabilizers and anti-foam agents.

The ash-containing detergents are exemplified by oil-soluble neutral and basic salts of alkali or alkaline earth metals with sulfonic acids, carboxylic acids, or organic phosphorus acids characterized by at least one direct carbon-to-phosphorus linkage such as those prepared by the treatment of an olefin polymer (e.g., polyisobutene having a molecular weight of 1000) with a phosphorizing agent such as phosphorus trichloride, phosphorus heptasulfide, phosphorus pentasulfide, phosphorus trichloride and sulfur, white phosphorus and a sulfur halide, or phosphorothioic chloride. The most commonly used salts of such acids are those of sodium, potassium, lithium, calcium, magnesium, strontium and barium.

The term "basic salt" is used to designate metal salts wherein the metal is present in stoichiometrically larger amounts than the organic acid radical. The commonly employed methods for preparing the basic salts involve heating a mineral oil solution of an acid with a stoichiometric excess of a metal neutralizing agent such as the metal oxide, hydroxide, carbonate, bicarbonate, or sulfide at a temperature above 50°C. and filtering the resulting mass. The use of a "promoter" in the neutralization step to aid the incorporation of a large excess of metal likewise is known. Examples of compounds useful as the promoter include phenolic substances such as phenol, naphthol, alkylphenol, thiophenol, sulfurized alkylphenol, and condensation products of formaldehyde with a phenolic substance; alcohols such as methanol, 2-propanol, octyl alcohol, cellosolve, carbitol, ethylene glycol, stearyl alcohol, and cyclohexyl alcohol; and amines such as aniline, phenylenediamine, phenothiazine, phenyl-$\beta$-naphthylamine, and dodecylamine. A particularly effective method for preparing the basic salts comprises mixing an acid with an excess of a basic alkaline earth metal neutralizing agent, a phenolic promoter compound, and a small amount of water and carbonating the mixture at an elevated temperature such as 60–200°C.

Ashless detergents and dispersants are illustrated by the interpolymers of an oil-solubilizing monomer, e.g., decyl methacrylate, vinyl decyl ether, or high molecular weight olefin, with a monomer containing polar substituents, e.g., aminoalkyl acrylate or poly-(oxyethylene)-substituted acrylate; the amine salts, amides, and imides of oil-soluble monocarboxylic or dicarboxylic acids such as stearic acid, oleic acid, tall oil acid, and high molecular weight alkyl or alkenyl-substituted succinic acid. Especially useful as ashless detergents are the acylated polyamines and similar nitrogen compounds containing at least about 54 carbon atoms as described in U.S. Pat. No. 3,272,746; reaction products of such compounds with other reagents including boron compounds, phosphorus compounds, epoxides, aldehydes, organic acids and the like; and esters of high molecular weight carboxylic acids as described in U.S. Pat. Nos. 3,381,022 and 3,542,678.

Extreme pressure agents and corrosion-inhibiting and oxidation-inhibiting agents are exemplified by chlorinated aliphatic hydrocarbons such as chlorinated wax; organic sulfides and polysulfides such as benzyl disulfide, bis(chlorobenzyl) disulfide, dibutyl tetrasulfide, sulfurized sperm oil, sulfurized methyl ester of oleic acid, sulfurized alkylphenol, sulfurized dipentene, and sulfurized terpene; phosphosulfurized hydrocarbons such as the reaction product of a phosphorus sulfide with turpentine or methyl oleate; phosphorus esters including principally dihydrocarbon and trihydrocarbon phosphites such as dibutyl phosphite, diheptyl phosphite, dicyclohexyl phosphite, pentyl phenyl phosphite, dipentyl phenyl phosphite, tridecyl phosphite, distearyl phosphite, dimethyl naphthyl phosphite, oleyl 4-pentylphenyl phosphite, polypropylene (molecular weight 500)-substituted phenyl phosphite, diisobutyl-substituted phenyl phosphite; metal thiocarbamates, such as zinc dioctyldithiocarbamate, and barium heptylphenyl dithiocarbamate; Group II metal phosphorodithioates such as zinc dicyclohexylphosphorodithioate, zinc dioctylphosphorodithioate, barium di(heptylphenyl) phosphorodithioate, cadmium dinonylphosphorodithioate, and the zinc salt of a phosphorodithioic acid produced by the reaction of phosphorus pentasulfide with an equimolar mixture of isopropyl alcohol and n-hexyl alcohol.

An illustrative lubricating composition of this invention consists of mineral oil containing 6.25% by weight of the product of Example 6, 0.97% of a basic calcium alkylbenzenesulfonate, 0.84% of the zinc salt of a mixture of diisobutyl- and di-(primary amyl)phosphorodithioic acids, 0.50% of sulfurized n-butyl 2-cyclohexenecarboxylate, 0.17% of an interpolymer of a $C_{12-14}$ dialkyl fumarate, vinyl acetate and ethyl vinyl ether, and 0.004% of a silicone anti-foam agent.

What is claimed is:

1. An oil-soluble interpolymer comprising (A) at least about 50% by weight of units derived from a polymerizable alkyl ester of an unsaturated acid in which the alkyl group contains at least about 8 carbon atoms, said interpolymer also containing (B) units derived from a monomer of the formula

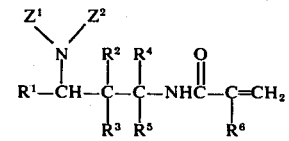

wherein each of $R^1$, $R^2$ and $R^3$ is hydrogen or a hydrocarbon or substituted hydrocarbon radical; each of $R^4$ and $R^5$ is a hydrocarbon or substituted hydrocarbon radical; $R^6$ is hydrogen or a lower alkyl or substituted lower alkyl radical; $Z^1$ is hydrogen or a hydrocarbon or substituted hydrocarbon radical and $Z^2$ is hydrogen or an alkyl, cycloalkyl or substituted alkyl or cycloalkyl radical,

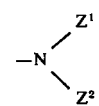

is a monocyclic or bicyclic heterocyclic radical in which the only hetero-atoms are nitrogen or nitrogen and oxygen.

2. An interpolymer according to claim 1 wherein the A units are derived from an alkyl acrylate or methacrylate.

3. An interpolymer according to claim 2 wherein each of $R^1$, $R^2$ and $R^3$ is hydrogen or a lower alkyl radical, each of $R^4$ and $R^5$ is a lower alkyl radical, $R^6$ is hydrogen and each of $Z^1$ and $Z^2$ is a lower alkyl radical.

4. An interpolymer according to claim 3 wherein said A units comprise at least 75% of said polymer with the balance being said B units.

5. An interpolymer according to claim 4 wherein $R^1$, $R^2$ and $R^3$ are hydrogen and $R^4$, $R^5$, $Z^1$ and $Z^2$ are methyl.

6. An interpolymer according to claim 4 wherein said A units are derived from isodecyl acrylate.

7. An interpolymer according to claim 6 wherein $R^1$, $R^2$ and $R^3$ are hydrogen and $R^4$, $R^5$, $Z^1$ and $Z^2$ are methyl.

* * * * *

UNITED STATES PATENT AND TRADEMARK OFFICE
CERTIFICATE OF CORRECTION

PATENT NO. : 3,979,441
DATED : September 7, 1976
INVENTOR(S) : Donald Irvin Hoke It is certified that error appears in the above-identified patent and that said Letters Patent are hereby corrected as shown below:

In column 10, line 49, --or-- should appear after "radical,".

Signed and Sealed this

Twenty-eighth Day of December 1976

[SEAL]

Attest:

RUTH C. MASON
*Attesting Officer*

C. MARSHALL DANN
*Commissioner of Patents and Trademarks*